United States Patent [19]

Haugland et al.

[11] Patent Number: 5,514,710

[45] Date of Patent: May 7, 1996

[54] PHOTOCLEAVABLE DERIVATIVES OF HYDROXYPRENESULFONIC ACIDS

[75] Inventors: Richard P. Haugland, Eugene; Kyle R. Gee, Springfield, both of Oreg.

[73] Assignee: Molecular Probes, Inc., Eugene, Oreg.

[21] Appl. No.: 180,543

[22] Filed: Jan. 11, 1994

[51] Int. Cl.$^6$ .................. A61K 31/265; A61K 31/185; C07C 309/38; C07C 69/96

[52] U.S. Cl. .................. 514/512; 514/576; 514/577; 558/270; 558/271; 562/45; 562/46; 562/70; 562/71; 562/72; 549/453; 549/454

[58] Field of Search .................. 562/45, 46, 70, 562/71, 72; 558/270, 271; 514/512, 576, 577; 549/453, 454

[56] References Cited

U.S. PATENT DOCUMENTS

| | | |
|---|---|---|
| 4,844,841 | 7/1989 | Koller et al. .................. 562/55 |
| 5,132,432 | 7/1992 | Haugland et al. .................. 548/518 |

FOREIGN PATENT DOCUMENTS 9005916  5/1990  WIPO.

OTHER PUBLICATIONS

Wolfbeis, et al. Anal. Biochem., 129,365 (1983).
Lempert, et al., Paper No. AIAA–93–0517, 31st Aerospace Sciences Meeting & Exhibit, Jan. 11–14, 1993, Reno NV.
Krafft, et al., J. Am. Chem. Soc., 110,301 (1988).
Enomoto, et al., Cancer Research, 44,5200 (1984).
Turner, et al., J. Am. Chem. Soc., 110, 224 (1988).
Barltrop, et al., Chemical Communications, 22, 822 (1966).
Sheehan, et al., J. Am. Chem. Soc, 86, 5377 (1964).

*Primary Examiner*—Glennon H. Hollrah
*Assistant Examiner*—Mary C. Cebulak
*Attorney, Agent, or Firm*—Allegra J. Helfenstein; Anton E. Skaugset

[57] ABSTRACT

The invention describes the synthesis and use of photoactivated (or caged) fluorescent dyes. Upon illumination at less than about 400 nm the caged dyes release highly fluorescent, water soluble hydroxypyrenesulfonic acid dyes according to the following equation:

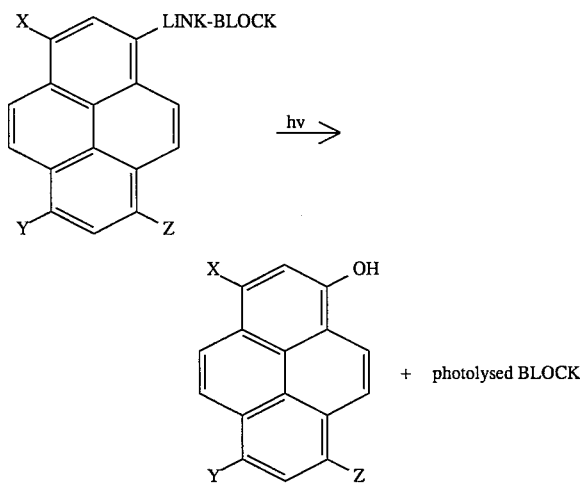

X, Y, and Z are independently sulfonic acid, a sulfonic acid salt, a hydroxyl group, or hydrogen, with at least one of X, Y, and Z being a sulfonic acid or sulfonic acid salt. LINK is either an ether linkage or a carbonate linkage. BLOCK is a caging group whose photolysis results in liberation of a free hydroxypyrenesulfonic acid dye.

The caged fluorescent dyes are useful for application in aqueous solutions, including fluids of biological origin. The caged dyes of the present invention are especially useful for flow tagging velocimetry.

17 Claims, 2 Drawing Sheets

PHOTOCLEAVABLE DERIVATIVES OF HYDROXYPRENESULFONIC ACIDS

This invention was made with U.S. Government support under research contract no. DAAH01-92-C-R224 awarded by the Defense Advanced Research Projects Agency (an agency of the Department of Defense). The U.S. Government has certain rights in this invention.

FIELD OF THE INVENTION

This invention relates to novel water-soluble derivatives of pyrenesulfonic acid that contain a photolabile blocking group. Upon photolysis these derivatives release water-soluble fluorescent dyes that have emission spectra measurably different from that of the starting materials. These materials are useful for following the flow of water and water-containing fluids.

BACKGROUND

The materials described in this invention belong to a class of materials known as photoactivatable or "caged" probes. The term "cage" refers to a photolytically sensitive substituent that is designed to maximally interfere with the reactivity or other physical properties of the free probe. Flash photolysis of the "caged" probe causes an intramolecular reaction of the substituent, and releases the free, or uncaged, probe. Because the appearance of the free probe can be so carefully controlled, caged probes provide a means of controlling the release—both spatially and temporally—of the active product or reagent.

When the probe that is bound to a photoreactive group is highly colored or fluorescent, the blocked probe is known as a "caged" dye. Generally caged dyes are useful in that only the blocked precursor is present until illumination, whereupon the active dye or marker is produced. In the case of caged fluorescent dyes, the blocked precursors are generally non-fluorescent, slightly fluorescent, or have fluorescence that occurs at substantially shorter wavelengths than that of the corresponding free dye. Illumination of the blocked precursor then liberates a pulse of highly fluorescent dye. The blocked precursor can be added to a sample or sample stream and allowed to reach the target area, but only upon photolysis is the desired fluorescent dye produced in the illuminated area. Following photolytic illumination, the subsequent migration, diffusion, photobleaching, or localization of the dye can be observed as a function of the time and location since photolysis.

The use of a chemical blocking group that is removable by photolysis has been widely used and described using a variety of materials. A typical blocking group used for this purpose is o-nitroarylmethine. Upon photolysis with light that includes wavelengths less than about 400 nm, the o-nitroarylmethine group is intramolecularly converted to a derivative of an o-nitrosophenone. Fluorophores that have been protected using the o-nitroarylmethine caging group include various hydroxy and amino derivatives of anthracenes, naphthalenes, coumarins, fluorescein, resorufin, and rhodamine. Known caged fluorophores are lipophilic dyes that are not water soluble, and are consequently not useful for following the flow of water and water-containing fluids. The use of these caged fluorescent dyes is therefore limited to organic media.

The compounds of the present invention are caged derivatives of hydroxypyrenesulfonic acids. Unlike most commonly used fluorophores, pyrenesulfonic acids are fluorescent dyes that possess high water solubility, in addition to high absorbance and high fluorescence quantum yield. These properties make hydroxypyrenesulfonic acid dyes ideal fluorescent dyes for use with biological materials, as well as other aqueous systems.

Chemically reactive fluorescent pyrenyloxysulfonic acids are described in U.S. Pat. No. 5,132,432 by Haugland et al. (1992). Derivatives of pyrenesulfonic acids containing long alkyl chains for use as lipid probes are described in U.S. Pat. No. 4,844,841 by Koller et al. (1989). Neither the Haugland nor the Koller patent describes pyrenesulfonic acids containing photoremovable blocking groups. Esters of hydroxypyrenesulfonic acids have been prepared wherein the ester substituent can be cleaved from the hydroxypyrenesulfonic acid dye by enzyme action (Woltbeis et al., *ANAL. BIOCHEM.*, 129, 365 (1983)). It is known that attaching this type of blocking group (a phosphate or an ester of an aliphatic carboxylic acid) to the hydroxyl group of 8-hydroxypyrene-1,3,6-trisulfonic acid shifts the absorption and fluorescence properties of the dye to noticeably shorter wavelengths. These derivatives do not contain photocleavable blocking groups, and have only been used to assay for the activity of various hydrolases.

Caged dyes utilizing fluorophores other than pyrenes have been chemically attached to water-soluble materials such as proteins and dextrans to detect protein movement and assembly inside living cells and to follow water flow. The caged fluorophores of the present invention have the advantage of being intrinsically water soluble without further modification, having a higher yield of fluorescent product on a per weight basis, and also liberate highly water soluble fluorescent products. Additionally, in contrast to other caged fluorophores, the caged hydroxypyrenesulfonic acid dyes of the present invention are uncaged very quickly when photolytically illuminated, allowing very precise spatial and temporal control of the appearance of free fluorescent dye. For example, in order to generate the most fluorescent form of fluorescein from a typical caged fluorescein compound, photolysis of two individual caging moieties is required, whereas in the compounds of the present invention, only one caging moiety needs to be photolysed to generate maximal fluorescence.

The caged dyes of the present invention exhibit particular utility for the study of flow dynamics in aqueous systems. Generally, flow analysis and velocimetry have previously been performed by injecting a dye or marker into the water flow under study. These techniques can only reveal the most general information about the flow dynamics of such systems. The use of free fluorescent dyes allows the dye marker to be homogeneously dispersed throughout the flow stream, and flow data can be gathered by interrogating the water stream using excitation illumination, allowing a degree of accuracy in measuring flow and dynamics. The use of photoactivated fluorescent dyes, however, allows even greater control over the appearance of the active, uncaged, fluorescent dye that is used as a marker (or "tagging" agent). Nevertheless, even with caged fluoresceins (for example), the rate of uncaging upon photolysis illumination is slow enough to limit the accuracy of velocimetric data gathered using these probes. Because the photoactivated hydroxypyrenesulfonic acid dyes, in contrast, uncage very quickly upon photolysis illumination, the dyes of the present invention allow a fluorescent label to be generated within the water stream with precise control of both time zero and space zero (the exact time and place that fluorescent marker initially appears in the stream).

The use of a caged pyrenetrisulfonic acid dye of the present invention in the evaluation of hydrodynamic flow around a lifting surface is described in Lempert et al., Paper No. AIAA-93-0517, 31st Aerospace Sciences Meeting & Exhibit, Jan. 11–14, 1993, Reno Nev. A caged fluorescein-dextran conjugate is also described in the above paper as useful for flow tagging. The non-polar character of the fluorescein fluorophore requires the conjugation of the dye to a dextran to give it the necessary water solubility for this use. As the caged pyrenesulfonic acid is completely water soluble, it can be utilized at a concentration of 5 mg/L, while the caged fluorescein-dextran can only be utilized at a concentration of 2 mg/L. The lower concentration of fluorescein conjugate, combined with the greater mass of the conjugate due to the presence of the bulky dextran, results in much lower concentration of fluorescent moieties that can be formed following photolysis within the flow stream.

DESCRIPTION OF THE INVENTION AND SUMMARY OF PREFERRED EMBODIMENTS

The compounds of the present invention are caged fluorophores that upon photolysis release water-soluble, highly fluorescent hydroxypyrenesulfonic acid dyes.

The compounds of the present invention are substituted pyrenes that can be described by the general formula:

X, Y, and Z are independently sulfonic acid, a sulfonic acid salt, a hydroxyl group, or hydrogen, with at least one of X, Y, and Z being a sulfonic acid or sulfonic acid salt. Typically all three of X, Y and Z are sulfonic acid groups. The salts of the sulfonic acid groups can be any cations that retain sufficient solubility of the free dye in water to permit its detection in a sample. Typically, sufficient water solubility for the compounds of the present invention is considered to be solubility of the free dye in water exceeding 0.1 mg/mL. More preferably the solubility of the free dye in water exceeds 1 mg/mL. In one embodiment of the invention, the counterions of the sulfonic acid groups are alkali metal cations. In another embodiment of the invention, the counterions are ammonium ions, alkylammonium ions, polyalkylammonium ions, alkoxyammonium ions, or polyalkoxyammonium ions, the alkyl portions of each containing 1–6 carbon atoms. Preferably the sulfonic acid salts are $Li^+$, $K^+$, $Na^+$, $NH_4^+$, $NBu_4^+$.

CAGE is a group that, upon photolytic illumination, undergoes an irreversible reaction to liberate a free hydroxypyrenesulfonic acid dye. It is generally useful to describe CAGE in two parts, the linking group LINK, and the blocking group BLOCK, as shown in the formula:

LINK is selected such that photolytic cleavage of the BLOCK group results in the formation of a hydroxy group on the pyrenesulfonic acid moiety. LINK is either an oxygen atom (—O—) that is covalently bound to both the pyrene and BLOCK to create an ether linkage, or alternatively, LINK is a bridging $CO_3$ group that is covalently bound to both the pyrene and BLOCK to create to give a carbonate linkage (—O—(C=O)—O—).

The pyrene moiety is covalently attached to BLOCK by the LINK moiety. The photolysis of BLOCK results in liberation of a free hydroxypyrenesulfonic acid dye. In one embodiment of the invention, BLOCK is a derivative of o-nitroarylmethine described by the formula B(1):

The substituent $R^1$ is hydrogen, carboxylate (—$CO_2H$), an alkyl group having 1–6 carbons, an unsubstituted aromatic group, or an aromatic group substituted by —$NO_2$, —$OR^3$, or —$(CH_2)_n$—$CO_2$—M, where $R^3$ is an alkyl group having 1–6 carbons, n=0–3, and M is either $Li^+$, $Na^+$, $K^+$, or $NH_4^+$. Preferably $R^1$ is H or an aromatic group. The aromatic ring A of B(1) is optionally independently further substituted 1–2 times by —$NO_2$, or alkoxy having 1–6 carbons. Alternatively, two adjacent aromatic positions can be substituted by a methylenedioxy moiety; or two adjacent ring substituents taken in combination form a six membered aromatic ring, making A a naphthyl structure. Preferably the aromatic ring A of B(1) is substituted by alkoxy having 1–6 carbons or —$NO_2$.

In another embodiment, BLOCK is a derivative of arylaroylmethine described by the formula B(2):

Aromatic rings B and C of B(2) are optionally independently substituted one or more times by halogen, —$NO_2$, —$OR^4$, and —$NR^5R^6$, where $R^4$, $R^5$ and $R^6$ are independently alkyl groups having 1–6 carbons. Preferably there are no more than two substituents on each of rings B and C.

In an additional embodiment of the invention, BLOCK is described by the formula B(3):

The blocking group B(3) is bound to LINK via a carbonyl linkage, and when BLOCK is of the formula B(3), LINK must be —O—, and cannot be —O—(C=O)—O—. The substituent $R^7$ is hydrogen or methyl, typically methyl. The substituent $R^2$ is H, —OH, —OR$^4$, or —NR$^5$R$^6$, where —OR$^4$ and —NR$^5$R$^6$ are as described above. Preferably $R^2$ is —NR$^5$R$^6$.

Preferably BLOCK is described by the formula B(1) or B(2), more preferably B(1).

Upon photolysis at less than about 400 nm, the compounds of the present invention undergo a intramolecular conversion to give a water-soluble hydroxypyrenesulfonic acid dye (Eq. 1).

In particular, when BLOCK is of the formula B(1), the photolytic intramolecular cleavage of the BLOCK group is depicted in Eq. 2.

When LINK is a carbonate linking group, photolysis of the compound yields a carbonic acid monoester of the pyrene. This monoester is unstable and rapidly and spontaneously decarboxylates to give the same photolysis products as compounds which possess an ether LINK.

BLOCK is typically selected such that the caged dye has substantially different spectral properties than that of the free hydroxypyrenesulfonic acid dye. Generally the presence of the BLOCK group will reduce the fluorescence of the pyrenesulfonic acid group; preferably the fluorescence will be completely quenched. Typically the presence of the BLOCK group will shift the longest wavelength absorbance of the conjugate toward the blue region of the spectrum, preferably to less than about 400 nm. Illumination at wavelengths less than about 400 nm is considered photolytic illumination, and results in the photocleavage of BLOCK, and the release of a free hydroxypyrenesulfonic acid.

The photolabile group BLOCK can be substituted further so as to confer improved absorbance properties, enhance the rate of photolysis, or improve other properties of the caged dye. For instance, in the case where BLOCK is of the formula B(1) it is known that substitution of lower alkoxy and nitro groups onto the aromatic ring, or substitution of R by lower alkyl, carboxylate, or aryl can have beneficial effects on the rate of photolysis. The effect of substitutions of BLOCK on the photolysis rate of the compounds of the present invention can be tested by photolysing the substituted compound and observing the rate of formation of a fluorescent product that can be excited at about 420 nm or longer wavelength. When the pH of an aqueous solution containing both the caged and photolysed dyes is sufficiently high to ionize the phenolic moiety of the free dye (typically pH >7), the excitation absorbance and emission maxima of the free hydroxypyrenesulfonic acid typically occurs at a significantly longer wavelength than that of the protected dye.

In one embodiment of the invention, the caged fluorophores described above are dissolved in an aqueous medium. The aqueous medium can be a pure solution of water, or a solution of water with other dissolved or suspended substances. The caged dyes of the present invention are also useful in non-aqueous solvents, such as methanol or acetone, if the polarity of the solvent is high enough to provide sufficient solubility.

In one aspect of the invention, the aqueous medium is a stream of fluid that is under analysis to determine the flow dynamics and velocity of the stream. Alternatively, the aqueous medium is a fluid sample in a cuvette or spectrophotometer cell, and illumination, excitation, and detection of the fluorescence of the sample is being performed to evaluate the dyes of the present invention.

In another embodiment, the aqueous medium is a fluid of biological origin. The biological fluid is optionally contained in a biological system (in vivo) or in a container (in vitro). Appropriate biological fluids include, but are not limited to, urine, cerebrospinal fluid, blood, lymph fluids, mucous, saliva, or physiological secretions; interstitial fluids, intra- or intercellular fluids such as cytoplasm.

After dissolution in the appropriate medium, the compounds of the present invention are photolysed to cleave the blocking group and produce a free hydroxypyrenesulfonic acid dye. This photolytic illumination will typically have a wavelength of less than 400 nm, preferably less than 360 nm. Although the photolytic illumination will typically have a wavelength greater than 200 nm, in order to prevent damage to biological systems (when present) the illumination will preferably have a wavelength greater than 300 nm. The photolysis illumination of compounds of the present invention is completely analogous to photolysis procedures known in the art for other caged probes, and is well known to one of ordinary skill. Illumination of the caged compound within the absorption bands of BLOCK is required, typically using a light source capable of radiation at less than about 400 nm. Typical light sources include mercury arc lamps, flash lamps and lasers such as nitrogen lasers. The photolytic illumination is typically generated using an ultra-violet laser. Photolysis of a solution of a compound of the present invention will typically produce a mixture of caged and free hydroxypyrenesulfonic acid dyes.

After uncaging, the free hydroxypyrenesulfonic acid dyes possess strong fluorescence. Illumination at or near the absorbance maximum of the free dye will produce the greatest fluorescent emission. Typically, maximal long wavelength absorbance of the free dye is between 420 and 480 nm. Fluorescence emission can be excited at any wavelength at which the photolysis product absorbs, but the fluorescent dye is preferably excited at a wavelength that is longer than the longest wavelength absorbance of the caged precursor.

Figure 1:
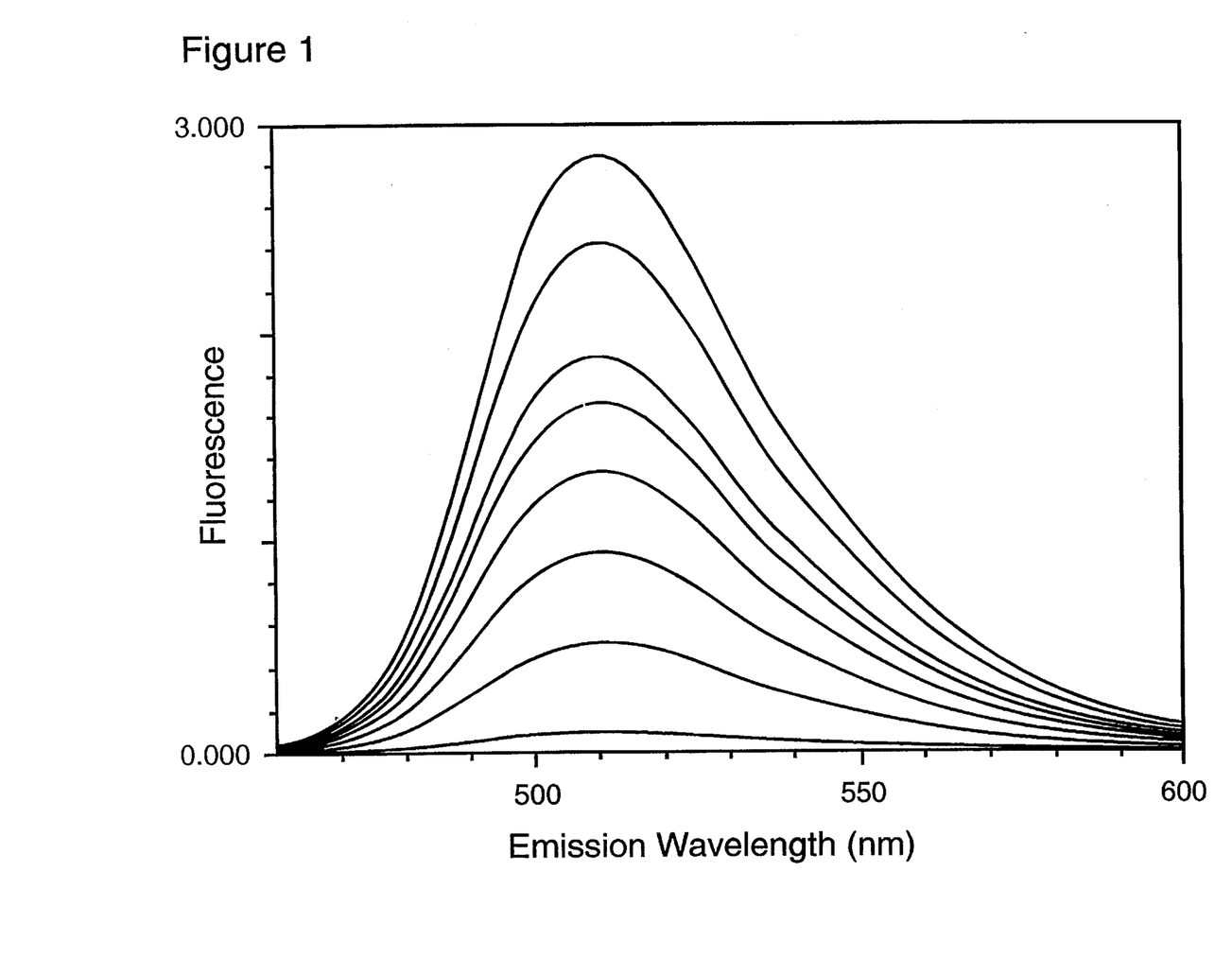
FIG. 1: The increase in fluorescent emission of a solution of 8-(4,5-dimethoxy-2-nitrobenzyloxy)pyrene-1,3,6-trisulfonic acid as a function of the duration of photolytic illumination. Photolyric illumination was at 360±10 nm. Fluorescence illumination occurred at 454±2 nm. Spectra were recorded after 0, 2, 4, 6, 8, 10, 15 and 20 minutes of photolysis illumination. The solution was illuminated in a fluorometer, in a 1 cm pathlength cuvette.

The resulting fluorescence is detected by visible inspection, using photographic film, or by measurement with a suitable apparatus such as a fluorometer, a fluorescence microscope, a fiber optic sensor, a photomultiplier tube, a plate reader, or a flow cytometer. The fluorescence emission can be detected at wavelengths greater than 470 nm and less than 600 nm, preferably at wavelengths greater than 500 nm and less than 530 nm. The kinetics of photolysis of the compounds of the present invention are conveniently followed by detecting the fluorescence of the compounds at about 510 nm after excitation illumination at about 450 nm, where the caged dye typically has low absorbance and virtually no fluorescence (See FIG. 1). If necessary, the quantum yield of photolysis can be determined by determining the moles of dye that are formed for a given number of photons of light as done by Krafft et al., *J. AM. CHEM. SOC.*, 110, 301 (1988).

Figure 2:
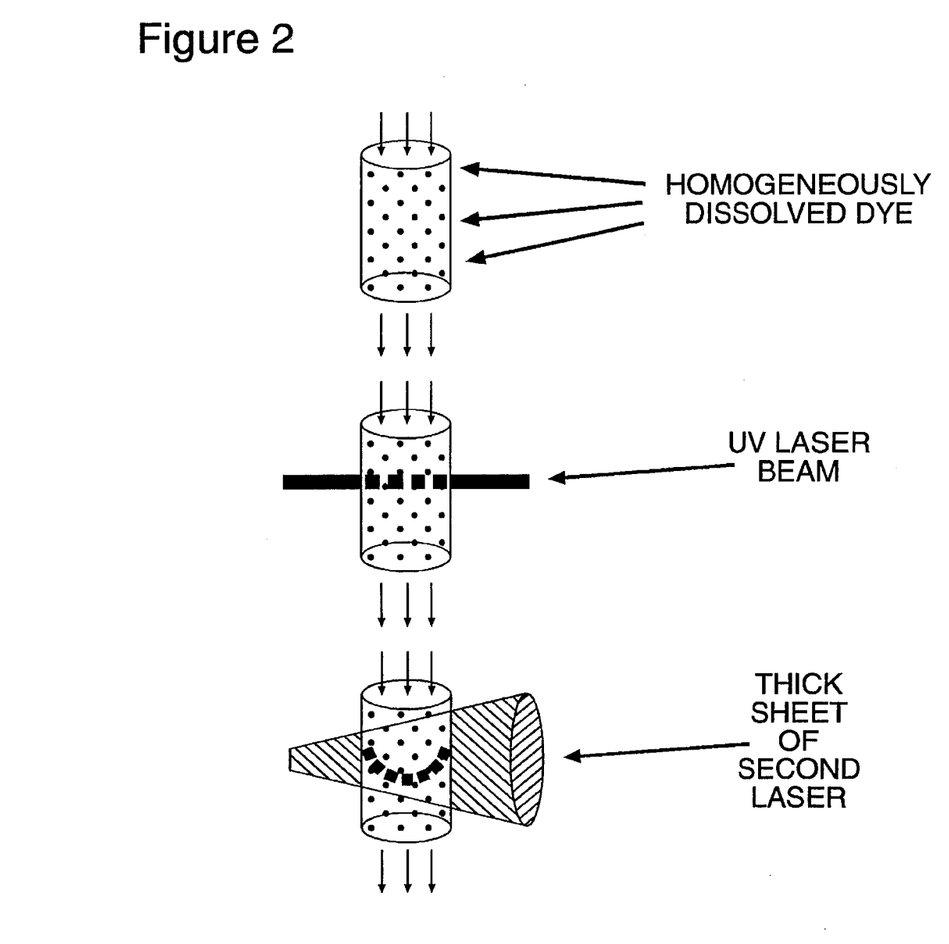
FIG. 2: A schematic illustration of the use of the present invention to determine flow velocity and flow dynamics in a water stream. A homogeneous solution of caged dye in an aqueous stream is photolytically illuminated to give a narrow pulse of free dye. The stream is then excited by fluorescence illumination and the location of the free dye molecules is determined by observation of the resulting fluorescent emission.

The caged dyes of the present invention are very useful for monitoring water flow to determine flow velocity and flow dynamics (See FIG. 2). In this application, a caged dye of the present invention is homogeneously dispersed in a water channel apparatus or pipe where the walls are transparent to UV and visible light. The fluid in the apparatus is essentially colorless and non-fluorescent. As the water is moving, a line or other pattern is "written" into the flow with a UV laser (photolysis illumination), the pattern depending solely on the optics of the illumination source, giving spatial and temporal control on the order of the UV pulse. The water in the apparatus is now fluorescent only where the UV laser interacted with the water, and this fluorescent pattern and its evolution via flow are detected downstream by illumination with a second laser at 425–490 nm, and the resulting fluorescence can be recorded on a normal video camera.

In addition to utility in static or flowing water systems, the compounds of the present invention are useful probes for biological systems. For example, the instant compounds are useful for lineage tracing in developing embryos. Thus an embryo is loaded with the blocked precursor before cellularization, and at the desired stage of development, individual cells are marked by illumination with a UV microbeam revealing the cellular lineage of the cells displaying fluorescence. Additionally, intracellular communication can be probed with the present invention using techniques that are entirely analogous to those that use tracers that are intrinsically fluorescent such as Lucifer Yellow CH (Enomoto et al., *CANCER RESEARCH*, 44, 5200 (1984)). Single cells are micro-injected with a caged hydroxypyrenesulfonic acid. UV microbeam illumination of adjacent cells connected to the injected cells by cell-to-cell junctional membrane channels uncages any caged precursors present in those cells, which will then become fluorescent. The amount of cell-to-cell exchange will be reflected by the amount of fluorescence present in adjacent cells. Those cells that are not connected will remain non-fluorescent after UV irradiation.

The dynamics of intracellular flow can also be probed using the present invention. A single cell can be indiscriminately loaded with a caged hydroxypyrenesulfonic acid, followed by UV microbeam illumination of a specific location compartment or organelle within the cell. This illumination releases free fluorescent dye with excellent spatial and temporal control. The subsequent cellular migration or flow of the fluorescent dye to other locations in the cell can be then determined using conventional fluorescence microscopy. The compounds of the present invention are particularly advantageous in this application, in that they are highly polar, whereas previously known caged fluorophores are largely non-polar, and tend to compartmentalize within cells.

Synthesis

The general synthetic scheme for the compounds of the present invention requires an appropriately substituted pyrene precursor and an appropriately substituted BLOCK precursor. The two precursors are then linked concomitant with the formation of the LINK moiety. The most common, and preferred, pyrene precursor is 8-hydroxypyrene-1,3,6-trisulfonic acid (also called pyranine or D&C Green #8). This precursor is not only commercially available, but it possesses high water solubility, a relative ease of modification to form stable ether or carbonate derivatives and useful spectral properties. Another particularly suitable precursor is 6,8-dihydroxypyrene- 1,3-disulfonic acid (LAMBDA FLUORESZENZ-TECHNOLOGIE, Graz, Austria). Specific methods for synthesizing selected compounds of the present invention can be found in the examples.

The examples below are given so as to illustrate the practice of this invention. They are not intended to limit or define the entire scope of this invention. Modifications of these methods and procedures that yield essentially the same or similar products would be readily apparent to one of ordinary skill in the art.

EXAMPLE 1

Preparation of
8-(4,5-dimethoxy-2-nitrobenzyloxy)pyrene-1,3,6-trisulfonic acid.

The following compound is prepared:

Commercially available 8-hydroxypyrene-1,3,6-trisulfonic acid, trisodium salt, is treated with strongly acidic ion exchange resin to give the free acid, which is then reacted with tetrabutylammonium hydroxide to give 8-hydroxpyrene-1,3,6-trisulfonic acid, tetrakis(tetrabutylammonium) salt (1).

The reaction of 4,5-dimethoxy-2-nitrobenzyl alcohol, carbon tetrabromide and triphenylphosphine is used to generate 4,5-dimethoxy-2-nitrobenzyl bromide, which is then treated with sodium iodide to give 4,5-dimethoxy-2-nitrobenzyl iodide (2).

To an amber solution of (1) (0.86 gm, 0.60 mmol) and (2) (0.234 g, 0.725 mmol) in chloroform (25 mL) at room temperature is added silver (I) oxide (0.185 g, 0.80 mmol). The resulting mixture is heated to reflux overnight under dim light. After cooling to room temperature, the mixture is filtered. The filtrate is concentrated in vacuo, and the concentrate is passed through a silica gel plug (35 g) using chloroform-methanol-triethylamine (6:3:1) as eluant. After collection of the eluant, the solvent is removed, leaving 1.2 g of a semi-solid amber oil, which is then passed through a strongly acidic ion exchange column (2×15 cm) using water as eluant and collecting 10 mL fractions. This cation exchange chromatography gives partial purification; the pure fractions are lyophilized to give 0.081 g of pure product. The impure fractions are lyophilized, and the residue is purified by passing through a column of Sephadex LH-20 (30 mL dry resin), using water as eluant. The pure fractions are combined and lyophilized to give the product as 0.114 g of a fluffy yellowhygroscopic powder (49% overall yield). The product is characterized by melting point determination (m.p. 154°–158° C., dec.), $^1$H NMR spectroscopy ($D_2O$) and UV-visible spectroscopy. Photogeneration of free dye from the product is demonstrated by qualitatively monitoring the rise in fluorescence (454 nm excitation, 505 nm emission) of a solution of the product upon photolysis at 360 nm. The desired salts of the compound are prepared by dissolution of the free sulfonic acid in water, followed by neutralization to pH~7 with an alkali metal hydroxide or amine, followed by lyophilization.

EXAMPLE 2

Preparation of
8-(2-oxo-1,2-diphenethyl-1-oxy)pyrene-1,3,6-trisulfonic acid.

The following compound is prepared:

To a solution of (1) (0.500 g, 0.351 mmol, described above) in chloroform (20 mL) at room temperature is added desyl bromide (0.102 g, 0.370 mmol) and silver (I) oxide (0.093 g, 0.40 mmol). The resulting mixture is stirred for 24 hours under dim light, and filtered. The filtrate is concentrated in vacuo to give a brown oil, which is passed through a strongly acidic ion exchange column using water as eluant. The product-containing fractions are then lyophilized to give 174 mg of an amber solid. This solid is then purified by chromatography on Sephadex LH-20 using water as eluant, to give the product as 116 mg of a yellow brown powder (51% yield). The product is characterized by $^1$H NMR spectroscopy ($d_6$-DMSO) and UV-visible spectroscopy. Photoactivated fluorescence is qualitatively monitored at 454/505 nm by observing the rise in fluorescence of a solution of the product upon photolysis at 360 nm.

EXAMPLE 3

Preparation of
8-(4,5-dimethoxy-2-nitrobenzyloxycarbonyl)pyrene-1,3,6-trisulfonic acid, tri(tetrabutylammonium) salt.

The following compound is prepared:

A solution of (2) (0.500 g, 0.351 mmol, prepared as described in Example 1) and 4,5-dimethoxy- 2-nitrobenzyloxycarbonyl chloride (0.110 g, 0.399 mmol, prepared from 4,5-dimethoxy-2-nitrobenzyl alcohol and phosgene) in chloroform (10 mL) is heated to reflux for 48 hours under dim light. The solvent is removed in vacuo, and the residue is purified by flash chromatography (22 g silica gel, elution with chloroform-methanol-triethylamine 9:1:0 to 60:35:5 to 5:4:1). The product fractions are pooled and concentrated, and the residue is then dissolved in dichloromethane. Filtration and concentration give the product as 365 mg of a pale yellow-green semi-solid (73% yield). The product is characterized by $^1$H NMR spectroscopy.

EXAMPLE 4

Preparation of
8-(o-hydroxy-α-methylcinnamoyl)pyrene-1,3,6-trisulfonic acid, tri(tetrabutylammonium) salt.

The following compound is prepared:

An aqueous solution of 1 (Example 1) and p-amidinophenyl-o-hydroxy-α-methylcinnamate, tosylate salt (Turner, et al., *J. AM. CHEM. SOC.*, 110, 244 (1988)) at pH 7.4 is treated to give the o-hydroxy-α-methylcinnamate conjugate of hydroxypyrenetrisulfonic acid, tetrakis(tetrabutylammonium) salt. The intermediate product is treated with an ion exchange resin to give the free sulfonic acid conjugate.

It is to be understood that, while the foregoing invention has been described in detail by way of illustration and example, numerous modifications, substitutions, and alter-

What is claimed is:

1. A compound of the formula wherein
at least one of X, Y, and Z is —SO$_3$H or —SO$_3$—SALT; the remainder of X, Y and Z are independently —SO$_3$H, —SO$_3$—SALT, —OH, or H; where SALT is an alkali metal cation, ammonium, alkylammonium, polyalkylammonium, alkoxyammonium, or polyalkoxyammonium ion, the alkyl portions of each independently containing 1–6 carbon atoms;
LINK is either —O— or —O—(C=O)—O—;
and BLOCK is described by the formula where R$^1$ is hydrogen, carboxylate (—CO$_2$H), an alkyl group having 1–6 carbons, or ARYL;
wherein ARYL is an unsubstituted phenyl, or phenyl substituted independently one or more times by —NO$_2$, —OR$^3$, where R$^3$ is an alkyl having 1–6 carbons; or —(CH)$_n$—CO$_2$—M, where n=0–3 and M is Li$^+$, Na$^+$, K$^+$, or NH$_4^+$;
the remaining positions on the aromatic ring A are optionally independently substituted one or more times by —NO$_2$, or —OR$^3$; or two adjacent positions on aromatic ring A, taken in combination, form a fused 6 membered ring to give a naphthyl structure; or substituents on two adjacent positions on aromatic ring A, taken in combination, form a methylenedioxy structure;
or BLOCK is described by the formula where the remaining positions on aromatic rings B and C are optionally independently substituted one or more times by halogen, —NO$_2$, —OR$^4$, and —NR$^5$R$^6$, where R$^4$, R$^5$ and R$^6$ are independently alkyl groups having 1–6 carbons;
or LINK is —O— and BLOCK is described by the formula wherein R$^7$ is H or Me; and R$^2$ is H, —OH, —OR$^4$, or —NR$^5$R$^6$.

2. A compound according to claim 1, wherein BLOCK is described by the formula where R$^1$ is hydrogen, carboxylate (—CO$_2$H), an alkyl group having 1–6 carbons, or ARYL;
wherein ARYL is an unsubstituted phenyl, or phenyl substituted independently one or more times by —NO$_2$, —OR$^3$, where R$^3$ is an alkyl having 1–6 carbons; or —(CH)$_n$—CO$_2$—M, where n=0–3 and M is Li$^+$, Na$^+$, K$^+$, or NH$_4^+$;
the remaining positions on the aromatic ring A are optionally independently substituted one or more times by —NO$_2$, —OR$^3$, or —(CH)$_n$—CO$_2$—M; or two adjacent positions on aromatic ring A, taken in combination, form a fused 6 membered ring to give a naphthyl structure; or substituents on two adjacent positions on aromatic ring A, taken in combination, form a methylenedioxy structure.

3. A compound according to claim 2, wherein LINK is —O—.

4. A compound according to claim 2, wherein X, Y, and Z are —SO$_3$H or —SO$_3$—SALT.

5. A compound according to claim 1, wherein BLOCK is described by the formula where R$^1$ is hydrogen, carboxylate (—CO$_2$H), an alkyl group having 1–6 carbons, or ARYL; wherein ARYL is an alkoxy or nitro-substituted phenyl.

6. A compound according to claim 1 of the formula wherein LINK is —O— or —O—(C=O)—O—; and
X, Y, and Z are —SO₃H or —SO₃—SALT.

7. A compound according to claim 1, wherein BLOCK is described by the formula where the remaining positions on aromatic rings B and C are optionally independently substituted one or more times by halogen, —NO₂, —OR⁴, and —NR⁵R⁶, where R⁴, R⁵ and R⁶ are independently alkyl groups having 1–6 carbons.

8. A compound according to claim 7, wherein LINK is —O— and X, Y, and Z are —SO₃H or —SO₃—SALT.

9. A compound according to claim 7, wherein BLOCK is described by the formula 10. A compound according to claim 1, wherein X, Y, and Z are —SO₃H or —SO₃—SALT;

LINK is —O—; and

BLOCK is described by the formula wherein R⁷ is H or Me; and R² is H, —OH, —OR⁴, or —NR⁵R⁶.

11. A mixture comprising an aqueous solution of a photoactive compound of the formula wherein at least one of X, Y, and Z is —SO₃H or —SO₃—SALT; the remainder of X, Y and Z are independently —SO₃H, —SO₃—SALT, —OH, or H; where SALT is an alkali metal cation, ammonium, alkylammonium, polyalkylammonium, alkoxyammonium, or polyalkoxyammonium ion, the alkyl portions of each independently containing 1–6 carbon atoms;

LINK is either —O— or —O—(C=O)—O—;

and BLOCK is described by the formula where R¹ is hydrogen, carboxylate (—CO₂H), an alkyl group having 1–6 carbons, or ARYL;

wherein ARYL is an unsubstituted phenyl, or phenyl substituted independently one or more times by —NO₂, —OR³, where R³ is an alkyl having 1–6 carbons; or —(CH)ₙ—CO₂—M, where n=0–3 and M is Li⁺, Na⁺, K⁺, or NH₄⁺;

the remaining positions on the aromatic ring A are optionally independently substituted one or more times by —NO₂, —OR³, or —(CH)ₙ—CO₂—M; or two adjacent positions on aromatic ring A, taken in combination, form a fused 6 membered ring to give a naphthyl structure; or substituents on two adjacent positions on aromatic ring A, taken in combination, form a methylenedioxy structure;

or BLOCK is described by the formula where the remaining positions on aromatic rings B and C are optionally independently substituted one or more times by halogen, —NO₂, —OR⁴, and —NR⁵R⁶, where R⁴, R⁵ and R⁶ are independently alkyl groups having 1–6 carbons;

or LINK is —O— and BLOCK is described by the formula wherein $R^7$ is H or Me; and $R^2$ is H, —OH, —OR$^4$, or —NR$^5$R$^6$;

wherein the concentration of said compound is greater than 10 nanogram per milliliter and less than 10 milligrams per milliliter.

12. A mixture according to claim 11, further comprising a fluorescent dye of the formula wherein the fluroescent dye is the photolysis product of said photoactive compound, and X, Y, and Z are as defined for said photoactive compound.

13. A mixture according to claim 12, wherein the fluorescent dye is formed by photolysis of said photoactive compound using light having a wavelength of less than about 400 nanometers.

14. A mixture according to claim 13, wherein the fluorescent dye, when illuminated by light at a wavelength greater than about 425 nanometers, fluoresces at a wavelength greater than about 480 nanometers.

15. A mixture according to claim 14, wherein the fluorescence of said fluorescent dye is detected at a site that is remote from the site of the photolysis of said photoactive compound and is performed at a time that is at least 1 microsecond subsequent to the time of photolysis.

16. A mixture according to claim 12, wherein the aqueous solution is a biological fluid.

17. A mixture according to claim 16, wherein the biological fluid is present within a living organism or cell.

* * * * *

UNITED STATES PATENT AND TRADEMARK OFFICE
CERTIFICATE OF CORRECTION

PATENT NO. : 5,514,710
DATED : May 7, 1996
INVENTOR(S) : Haugland et al.

It is certified that error appears in the above-indentified patent and that said Letters Patent is hereby corrected as shown below:

At col 9, line 15, "yellowhygroscopic" should be --yellow hygroscopic--.

At col 12, line 25, "R'" should be --$R^1$--.

Signed and Sealed this

Twentieth Day of August, 1996

Attest:

BRUCE LEHMAN

Attesting Officer        Commissioner of Patents and Trademarks